(12) United States Patent
Adams et al.

(10) Patent No.: US 8,110,368 B1
(45) Date of Patent: Feb. 7, 2012

(54) SYNUCLEIN GAMMA AS A BIOMARKER OF OBESITY AND OBESITY-RELATED DISORDERS

(75) Inventors: Sean H. Adams, Davis, CA (US); Pieter J. Oort, Davis, CA (US)

(73) Assignee: The United States of America Department of Agriculture, as represented by the Secretary of Agriculture, Washington, DC (US)

( * ) Notice: Subject to any disclaimer, the term of this patent is extended or adjusted under 35 U.S.C. 154(b) by 137 days.

(21) Appl. No.: 12/350,213

(22) Filed: Jan. 7, 2009

Related U.S. Application Data (60) Provisional application No. 61/019,500, filed on Jan. 7, 2008.

(51) Int. Cl.
*G01N 33/53* (2006.01)
(52) U.S. Cl. ........................................................ 435/7.1
(58) Field of Classification Search ........................ None
See application file for complete search history.

(56) References Cited

U.S. PATENT DOCUMENTS

2004/0128706 A1* 7/2004 Masliah et al. ................. 800/18

OTHER PUBLICATIONS

Liu, Cancer Research, 2005, vol. 65, Issue 17, pp. 7635-7643.*
Oort et al. (Journal of Nutrition, May 2008, vol. 138, vol. 5, pp. 841-848.*
Singh, Expert Opinion Therapeutic Targets, 2008, vol. 12, issue 1, pp. 59-68.*

* cited by examiner

*Primary Examiner* — Robert Landsman
*Assistant Examiner* — Ian Dang
(74) *Attorney, Agent, or Firm* — Howard V. Owens; John D. Fado; Leslie Shaw (57) ABSTRACT

Disclosed is a method of identifying γ-synuclein expression, as a biomarker for adiposity and adiposity related disorders. Identification of γ-synuclein expression includes agonists and antagonists thereof which may be used in pharmaceutical compositions for the treatment of adiposity related disorders.

2 Claims, 11 Drawing Sheets

SYNUCLEIN GAMMA AS A BIOMARKER OF OBESITY AND OBESITY-RELATED DISORDERS

This application claims priority to U.S. Provisional Patent Application Ser. No. 61/019,500, filed Jan. 7, 2008 which is herein incorporated by reference in its entirety.

FIELD OF THE INVENTION

The present invention relates to the use of γ-synuclein as a biomarker for adiposity as well as the targeting, screening or development of γ-synuclein agonists or antagonists.

BACKGROUND OF THE INVENTION

Metabolic diseases represent a serious public health concern worldwide. Obese and overweight individuals account for half or more of the population of the United States, and the incidence of obesity has risen at an alarming rate over the two decades. Compared to lean individuals, overweight persons are susceptible to an array of disorders, including heart disease, high blood pressure, Type II diabetes, insulin resistance, stroke, and others (Must et al., 1999). The etiology of excess weight gain is complex and incompletely understood. In persons developing overweight or obese conditions, environmental and genetic factors underlie an imbalance between appetite/caloric intake and energy expenditure. Thus, novel strategies that improve energy balance through modulation of appetite and/or metabolic rate are useful to correct relevant diseases including obesity-related disorders such as insulin resistance, diabetes, circulatory system anomalies, etc.

Strategies to thwart excessive adipose tissue growth and accretion may also help in the treatment of obesity, or in the treatment of other diseases associated with the presence of inappropriately high amounts of this tissue globally or locally (i.e., lipomas, phaeochromocytomas, hibernomas). Innovative clinical treatments, including improving the circulating or tissue levels of triglycerides, cholesterol, glucose, insulin, leptin or other metabolically-relevant molecules, that help normalize one or more of the altered factors concomitant with metabolic derangement would also have tremendous value.

Increased risks of mortality and morbidity associated with perturbations of metabolism are not confined to the obese, overweight, or diabetic states, however. Cachexia, the loss of appetite, leading to fewer calories eaten in comparison to caloric requirements, is a feature of numerous disease states, including certain cancers, some viral infections (i.e., acquired immunodeficiency syndrome, AIDS), or bacterial infections (i.e., during some stages of sepsis), and can result in loss of fat mass and lean body mass. Furthermore, conditions in which energy expenditure is abnormally elevated can benefit from novel modalities that modulate metabolism. In severe burns, for instance, the metabolic rate can rise almost two-fold, malting administration of appropriate nutrition a tremendous challenge (Goldstein and Elwyn, 1989; Kinney et al., 1970). The clinical prognosis is poor for patients who drift into negative energy balance in such disease states (Tisdale, 1997), or in those persons suffering from excessive fat loss body-wide or regionally (i.e., lipoatrophic and lipodystrophic disorders). Treatment of metabolic disease may be in part effected through the innovative use of certain molecules as drugs or as targets of pharmaceutical, nutritional, or other interventions.

There is also a pressing need to discover molecules that may be used in creative diagnostic and/or predictive strategies associated with metabolic disease. For instance, alterations in the expression of certain genes and proteins may underlie or mark the progression of metabolic diseases associated with adipose tissue amount or adipose tissue physiology, such as obesity, lipoatrophic diseases, etc. Thus, analysis of the expression of certain genes and proteins in afflicted patients compared to a healthy population will assist in unraveling the etiology and/or progression level of their disease, thereby helping in the design of effective therapeutic and preventive strategies. Healthy patients may be screened for expression in cases in which expression is altered prior to the onset of disease, thus allowing for pre-emptive treatments that can limit metabolic disease progression. Furthermore, changes in the gene or protein sequences (and/or other alterations such as methylation, acylation, phosphorylation, etc.) in certain populations may be associated with disease or risk toward developing disease. This illustrates the need to discover new genes and proteins relevant to metabolic disorders and whose sequences or alterations lead to biological changes that predispose to metabolic disease, or are in fact predictive of the progression of disease. Finally, knowledge of such unique genes and proteins at the expression or activity level will enable tracking of the efficacy of therapeutic modalities designed to treat metabolic diseases; as well as, the use of expression and sequence analysis to monitor or predict the outcome of other diseases associated with excessive fat accretion, or those associated with abnormal fat loss. Discovery of fat cell-abundant genes and proteins are especially attractive in this regard.

Thus an embodiment of the invention describes γ-synuclein as an adipocyte (fat cell) abundant factor, and use of the protein and γ-synuclein-encoding nucleic acids in treating or preventing metabolic diseases in humans that are associated with or responsive to fat tissue amount and/or adipose tissue functions. Novel evidence for an important role for γ-synuclein in modifying adipose tissue function is presented. The white and brown adipose tissue of mammals are known to play a central role in energy storage and metabolic signaling, thus impacting appetite, metabolic rate, and energy balance, and the white adipose tissue also implicated as an important inflammatory tissue. Based on its adipose-abundance and its clear induction during the white adipocyte differentiation process, responsiveness of its expression in adipocytes to agonism of the known metabolic regulator protein peroxisome proliferator activated receptor (PPAR), and shifted adipose tissue expression level in obese human subjects, γ-synuclein appears to have important utility as a drug and drug target to treat or prevent metabolic disease and related disorders, including those characterized by excessive adipose accretion or abnormally low adipose stores. Furthermore, γ-synuclein mRNA or protein abundance in patient tissues may be used to diagnose, monitor, and assess treatment efficacy of metabolic disorders associated with adiposity or γ-synuclein activity. Finally, γ-synuclein protein or nucleotide sequence polymorphisms, or distinct modifications of the gene, mRNA, or protein by non-genomic factors such as methylation, acylation, etc., may be used as predictive biomarkers of metabolic disease risk or disease progression.

Described herein is the correlation between expression patterns of γ-synuclein and leptin in fat cells, coupled to a protein chaperone role of γ-synuclein reported in other cell types, supporting the novel concept that γ-synuclein activity is associated with factors that regulate net leptin expression/production/secretion and/or leptin protein folding. Considering the well-established role of leptin in modulating whole-body metabolism and obesity phenotypes, the association between leptin and γ-synuclein indicates that one role of the latter is to regulate net activity of leptin and hence, would regulate leptin-associated biological pathways. Thus, γ-synuclein mRNA or protein abundance in patient tissues may be used to diagnose, monitor, and assess treatment efficacy of disorders associated with dysfunctional leptin expression, secretion, and/or activity.

In addition, γ-synuclein protein or nucleotide sequence polymorphisms, or distinct modifications of the gene, mRNA, or protein by non-genomic factors such as methylation, acylation, etc., may be used as predictive biomarkers of disease risk or disease progression for conditions related to altered leptin availability or activity.

SUMMARY OF THE INVENTION

An embodiment of the invention is the use of γ-synuclein as a biomarker for adiposity or adiposity related disorders.

Another embodiment of the invention is the screening of potential compounds which serve as agonists or antagonists of compounds targeting γ-synuclein.

A further embodiment of the invention is the use of γ-synuclein agonists or antagonists in the treatment of diseases associated with or responsive to γ-synuclein activity.

DEFINITIONS

As used herein:

"Antagonist" includes any molecule that partially or fully blocks, inhibits, or neutralizes a biological activity of γ-synuclein or γ-synuclein mRNA disclosed herein. In a similar manner, the term "agonist" is used in the broadest sense and includes any molecule that mimics a biological activity of a γ-synuclein or γ-synuclein mRNA polypeptide disclosed herein. Suitable agonist or antagonist molecules specifically include agonist or antagonist antibodies or antibody fragments, or fragments or amino acid sequence variants of γ-synuclein or γ-synuclein mRNA.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

DETAILED DESCRIPTION OF THE INVENTION

Our discoveries of Tusc5 (1) and γ-synuclein as proteins most strongly-expressed in peripheral nervous system (PNS) neurons and adipocytes illustrate that in addition to anatomical connectivity between the PNS and WAT, there appear to be certain functional pathways shared by these otherwise disparate systems. To our knowledge, an association between γ-synuclein activities and metabolism, obesity, or fat cell physiology has not been reported previously.

Mining of murine gene tissue expression patterns in the SymAtlas database (15) led to the novel finding that γ-synuclein, a well-established peripheral neuron marker also expressed in several CNS sites (16-20) and implicated in cancer progression and cell survival (see (21)), is strongly expressed in adipocytes. Considering its involvement with cancer progression and cell proliferation events, we hypothesized that adipocyte γ-synuclein would be down-regulated in fat by PPARγ agonism and up-regulated in obesity, since development of the latter involves WAT plasticity, and PPARγ is critical for promoting terminal differentiation of fat cells. Results using PPARγ agonists in 3T3-L1 adipocytes, and a survey of expression in WAT derived from non-obese and obese human cohorts support these concepts. Furthermore, a close association between expression of γ-synuclein and leptin was discovered, and in light of studies pointing to a chaperone role of γ-synuclein in other cell types, this supports the concept that γ-synuclein is associated with pathways regulating leptin expression/production/secretion and/or folding (thereby influencing whole-body metabolism and other functions of leptin). Our findings are consistent with the hypothesis that γ-synuclein is a PPARγ target gene with an important role in fat cell physiology and organismal biology.

An embodiment of the invention is the use of identification/recognition of γ-synuclein expression and/or gene or protein chemical modification (i.e., methylation, acylation, phosphorylation) as biomarkers for adiposity or adiposity related disorders. Abnormal adiposity is associated with a variety of diseases including diabetes, cardiovascular disease, neuropathy and others. Adipose tissue secretes various bioactive metabolites, such as leptin, insulin-like growth factor-I, transforming growth factor β, tumour necrosis factor α, angiotensin II, neurotrophins, growth factors, cytokines, fatty acids, and many other factors that may cross the blood-brain barrier and affect brain health and subsequent dementia (Gustafsen, Lancet Neurol., 5:713-20, 2006) and metabolic regulation.

Should tissue plasticity and cell survival properties of γ-synuclein manifest in adipocytes, it is anticipated that the protein plays a role in regulating such events as net fat cell turnover, transdifferentiation, adipocyte cell survival, and/or exit from the fully-differentiated, mature fat cell phenotype. WAT is malleable in terms of its component adipocyte phenotypes and fat cell numbers. The physiological and pathophysiological ramifications of WAT plasticity shifts in adipocyte size, thermogenic capacity, and ability to utilize glucose and accumulate lipid, which would have a profound impact on metabolism. The positive energy balance associated with obesity development, for instance, leads to increased adipocyte size coupled to an expansion of adipocyte numbers to accommodate the larger energy load (46). Studies by Loncar, Cinti, and others have highlighted phenotypic and morphological conversions ("transdifferentiation" events) in subpopulations of adipose cells, enabling these cells to acquire white adipocyte- or brown adipocyte-like characteristics, even without proliferation from pre-adipocyte precursors per se (see, e.g., (9; 47-50)). Some have suggested that mature, fully-differentiated adipocytes can "de-differentiate" such that these cells revert phenotypically to resemble adipocytes derived from earlier stages of the adipogenic program (51-56), and/or acquire proliferative potential (55;56). We consistently observed increased adipose expression of γ-synuclein mRNA in obese human subjects, which may signal increased WAT plasticity or engagement of anti-apoptotic pathways in fat cells as adaptational responses to a chronically high energy storage load. Leptin expression and secretion are also increased in obesity, and another function for γ-synuclein could be regulation of these events in response to changes in adiposity. WAT γ-synuclein mRNA expression was reduced following 3 weeks of weight loss in our obese subjects, a period in which calorie storage is reduced and WAT energy stores are mobilized. This indicates that γ-synuclein expression is responsive to metabolic cues and plane of nutrition.

Another embodiment of the invention is the screening of potential compounds which serve as agonists or antagonists of compounds targeting γ-synuclein.

Agonists or antagonists of human γ-synuclein can be incorporated into pharmaceutical compositions. Such compositions typically comprise the agonists or antagonists and a pharmaceutically acceptable carrier. A "pharmaceutically acceptable carrier" includes any and all solvents, dispersion media, coatings, antibacterial and antifungal agents, isotonic and absorption delaying agents, and the like, compatible with pharmaceutical administration (Gennaro, 2000). Preferred examples of such carriers or diluents include, but are not limited to, water, saline, Finger's solutions, dextrose solution, and 5% human serum albumin. Liposomes and non-aqueous vehicles such as fixed oils may also be used. Except when a conventional media or agent is incompatible with an active compound, use of these compositions is contemplated. Supplementary active compounds can also be incorporated into the compositions.

A pharmaceutical composition of the agonist or antagonist is formulated to be compatible with its intended route of administration, including intravenous, intradermal, subcutaneous, oral (e.g., inhalation), transdermal (i.e., topical), transmucosal, and rectal administration. Solutions or suspensions used for parenteral, intradermal, or subcutaneous application can include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampules, disposable syringes or multiple dose vials made of glass or plastic. The agonists or antagonists may be be to normal or altered (over or under) expression of γ-synuclein. The above mentioned formulations may be used in the treatment of adipose and adiposity related disorders as well as abnormal leptin secretion.

The pharmaceutical compositions containing agonists or agonists of γ-synuclein can be included in a kit, container, pack, or dispenser together with instructions for administration to treat a metabolic disorder or disease. When the invention is supplied as a kit, the different components of the composition may be packaged in separate containers and admixed immediately before use. Such packaging of the components separately may permit long-term storage without losing the active components' functions. Kits may also include reagents in separate containers that facilitate the execution of a specific test, such as diagnostic tests or tissue typing. Other containers may have two compartments that are separated by a readily removable membrane that upon removal permits the components to mix. Removable membranes may be glass, plastic, rubber, etc. Kits may also be supplied with instructional materials. Instructions may be printed on paper or other substrate, and/or may be supplied as an electronic-readable medium, such as a floppy disc, CD-ROM, DVD-ROM, Zip disc, videotape, laserdisc, audio tape, etc. Detailed instructions may not be physically associated with the kit; instead, a user may be directed to an internet web site specified by the manufacturer or distributor of the kit, or supplied as electronic mail.

A further embodiment of the invention is the use of γ-synuclein agonists or antagonists, or use of modalities that result in increased or decreased γ-synuclein activity, in the treatment of diseases associated with abnormal adiposity or dysfunctional adipose tissue physiology.

A further embodiment of the invention is the use of γ-synuclein agonists or antagonists, or use of modalities that result in increased or decreased γ-synuclein activity, in the treatment of diseases associated with abnormal leptin secretion, or those that are responsive to changes in leptin activity.

Materials & Methods

3T3-L1 Adipocyte Differentiation & PPARγ Agonist Studies. Results herein were generated using the samples described in our recently-published studies (1). Briefly, murine 3T3-L1 fibroblasts (ATCC, Manassas, Va.) grown to between 5-9 passages were induced to differentiate into adipocytes using a protocol similar to Farmer et al. (i.e., (22)). Two-day-confluent cells grown in high-glucose (25 mM) DMEM and 10% FBS (37° C., 5% $CO_2$) in 6-well rat tail collagen-coated plates were exposed to differentiation medium containing 10 μg/ml bovine insulin (~1.6 μM), 1 μM dexamethasone, and 0.5 mM 3-isobutyl-1-methylxanthine (IBMX) for 2 days. Cells were grown thereafter in maintenance medium (DMEM/10% FBS+2.5 μg/mL insulin). Cell culture media was replaced daily. Proof-of-principle studies tested the ability of the potent non-thiazoladinedione PPARγ agonist GW1929 (23) to regulate γ-synuclein gene expression at various points in the 3T3-L1 adipocyte differentiation and maturation process, as indicated. For these experiments, cells were cultured for the times and doses indicated in media containing vehicle (DMSO; 0.1% by vol.) or GW1929 (0.1% by vol.). RNA was prepared from 3T3-L1 adipocytes using Trizol-based methods for cell culture samples (Ambion, Austin, Tex.). RNA abundance and integrity were checked using a Nanoprop® ND-1000 Spectrophotometer (Nanoprop Technologies, Wilmington, Del.) and an Agilent 2100 bioanalyzer (Agilent, Foster City, Calif.) per manufacturer's instructions.

Gene Expression Analyses. RNA abundance of γ-synuclein and of other genes of interest were measured in 3T3-L1 adipocyte samples using quantitative real-time PCR, as described in detail previously (1). These assays utilized gene-specific TaqMan primers and FAM-MGB labeled probes (Assays-on-Demand®, Applied Biosystems Inc., Foster City, Calif.) and were run in duplicate or triplicate for each sample using an ABI 7900HT instrument. Primers/probe ABI identifiers for human reagents were γ-synuclein (Hs00268306 ml), leptin (Hs00174877 ml), and 11B-hydroxysteroid dehydrogenase (11β-HSD-1; Hs00194153 ml), and for mouse, γ-synuclein (Mm00488345 ml) and others described previously (1). Mouse and human tissue panel samples, and samples derived from non-obese and obese WAT (24) were assayed using a two-step process with preparation of cDNA from total RNA, followed by quantitative real-time PCR. Briefly, for each sample, cDNA was prepared from 1-5 µg of total RNA using Superscript III reverse transcriptase (Invitrogen, Carlsbad, Calif.) followed by RNAse-H treatment per manufacturer's instructions. Reactions were carried out in a 384-well format and contained: cDNA corresponding to 40 ng (tissue panels) or 2 ng (obese and lean human WAT samples) of original total RNA, 1× Master Mix (ABI Universal PCR Master Mix, Part #4304437), and 1× primer-probe mix (Note: pilot studies examining the range of linearity between PCR cycle number and template amount in human WAT samples revealed that as little as 2 ng/well could be used for γ-synuclein and 18S cDNAs). Cycle conditions were 95° C. 10 min., then 45 cycles of 95° C. for 15 sec/60° C. for 1 min. Amplification cycle number (Ct) of 18S for each sample was determined using commercial 18S primers and probe (ABI) to correct for template loading differences across all target genes (ΔCt method: ΔCt=sample Ct−18S Ct), and expression values were determined relative to control transcript levels using a mathematical formula as previously described (1).

Human WAT mRNA. Samples were derived from volunteers undergoing surgery or were obtained via subcutaneous (SC) biopsy before and after a very low calorie weight loss regimen, as previously-described (24-26). Briefly, for comparisons between lean and obese SC WAT and visceral adipose tissue (VAT, omental) samples from experiments described by Grino et al. (24), 10 non-obese and 12 obese (BMI 37.9±1.5 kg/m$^2$) were studied. VAT was collected in the course of laparoscopy or laparotomy for gastroplasty or gynecological procedures, and SC fat obtained in parallel from the abdominal region. mRNA prepared from these samples was transferred to the WHNRC for quantitative PCR analyses. WAT mRNA samples were also obtained by Clément and colleagues from a subset (n=21) of the morbidly obese adult women described by Cancello et al. (26), and results from those samples were compared with non-obese control samples (n=9). Matched SC and omental VAT mRNA samples were available from 20 of the obese subjects, and tested to compare depot-specific gene expression. In a second group of adult French obese women, SC biopsy before and after a very low calorie diet (VLCD)(25) enabled testing of the effects of weight loss on gene expression. Briefly, 12 obese women participating in the VLCD reduced their daily energy intake by one third (941±27 kcal per day with 35% protein, 20% lipids and 45% carbohydrates) for 21 days. None of the subjects had a familial or personal history of diabetes or were taking medications, and prior to the study all volunteers were at their peak weight and were not on a restrictive diet. Subjects were not involved in an exercise program. Abdominal subcutaneous fat specimens (~1 g) from the periumbelical region were obtained by needle aspiration under local anesthesia after an overnight fast before and after the dietary intervention in obese subjects, and in non-obese volunteers (n=7) used for comparison. All biopsies were washed in PBS and stored in RNALater preservative solution (Qiagen, Courtaboeuf, France) at −80° C. until analysis. Total RNA was extracted using the RNeasy total RNA Mini kit (Qiagen), and quantitative real-time PCR (TaqMan) using ABI primers and probes described above was performed by the INSERM U872 lab. For human WAT Western blot analysis (see below), a sample of subcutaneous WAT was obtained from the upper gluteal region of an adult female volunteer via needle biopsy under local lidocaine anesthesia. The sample was washed twice in cold PBS to clean the biopsy of blood and loose connective tissue, and flash-frozen prior to storage at −80° C. Clinical investigations were approved by the ethical committees of each participating center and were performed according to the Declaration of Helsinki.

γ-synuclein Western Blots and Immunohistochemistry (IHC). Western blot analyses of γ-synuclein protein in murine, rat, and human WAT samples were conducted using an anti-γ-synuclein antibody E-20 (Santa Cruz Biotechnology). Briefly, tissue samples were homogenized using MPER extraction reagent (Pierce) with HALT protease and phosphatase inhibitors (Pierce). Protein concentrations were quantitated using the BCA assay (Pierce). Forty micrograms of total protein were separated on a 12% Bis-Tris SDS gel (Invitrogen) using MES running buffer (Invitrogen). The proteins were transferred to PVDF membrane and immunoblotted with goat anti-γ-synuclein antibody (1:100) in PBST overnight. Specific signal was detected with a HRP-conjugated secondary antibody (1:10,000 donkey anti-goat HRP, sc-2020, Santa Cruz Biotechnology) and using Visualizer ECL reagent (Millipore). Blots were imaged using a Fluorochem 8800 instrument (Alpha Innotech). Samples of liver, retroperitoneal WAT, epididymal WAT, and subcutaneous WAT (inguinal region) for Western blot studies were obtained from three male B6D2F1 mice fed a 60% kcal high-fat diet (D12492, Research Diets, New Brunswick, N.J.) for 8 weeks. Animals were fasted ~4-6 hr prior to tissue harvest, killed under $CO_2$, and tissues flash-frozen prior to storage at −80° C. For IHC of murine fat tissue, dissected subcutaneous WAT from a 6 month old C57BL/6 female mouse was fixed, paraffin embedded and sectioned as described previously (19). Affinity purified SK32 rabbit polyclonal anti-γ-synuclein antibody (17) in a 1:50 dilution and Vecstain Elite detection kit (Vector Laboratories) were used for immunohistochemical detection of γ-synuclein on these sections. To demonstrate specificity of immunostaining, 1 ml of diluted SK23 antibody was preincubated with 10 µg of a synthetic 15-mer C-terminal peptide of mouse γ-synuclein that has been used as an immunogen for production of this antibody. All animal studies were conducted under protocols adhering to Animal Welfare Act Guidelines, approved by the Animal Care and Use Committees at UC, Davis (for Western blot samples) and Cardiff University (IHC study).

Materials. Insulin, dexamethasone, IBMX, and GW1929 were purchased from Sigma (St. Louis, Mo.), DMEM and FBS from Gibco/BRL (Invitrogen, Carlsbad, Calif.), and cell culture plates were purchased from Nunc (Rochester, N.Y.). Murine and human total RNA tissue panels were obtained from Clontech (Mountain View, Calif.), with human preadipocyte (stromal-vascular cells from WAT biopsy) and cultured and fresh adipocyte total mRNAs bought from Zenbio (Research Triangle Park, N.C.). Mouse epididymal WAT used in the mRNA tissue panel was from pooled adult C57BL/6J tissues.

Statistics. Changes in gene expression over time+/−PPARγ activation during 3T3-L1 adipogenesis was evaluated using a two-way ANOVA testing for significant effects of time, treatment, and time x treatment interaction (Prism 4.03 software; GraphPad, San Diego, Calif.). A similar approach was used to evaluate effects of obesity, WAT depot, and obesity x depot interactions, or to test obesity, sex, and obesity x sex interactions as relevant in human studies. Comparisons across two groups were done using a Student's t-test, or across 3 groups by ANOVA. Means±SEM are presented, and $p<0.05$ was considered statistically-significant.

Results

Figure 1:
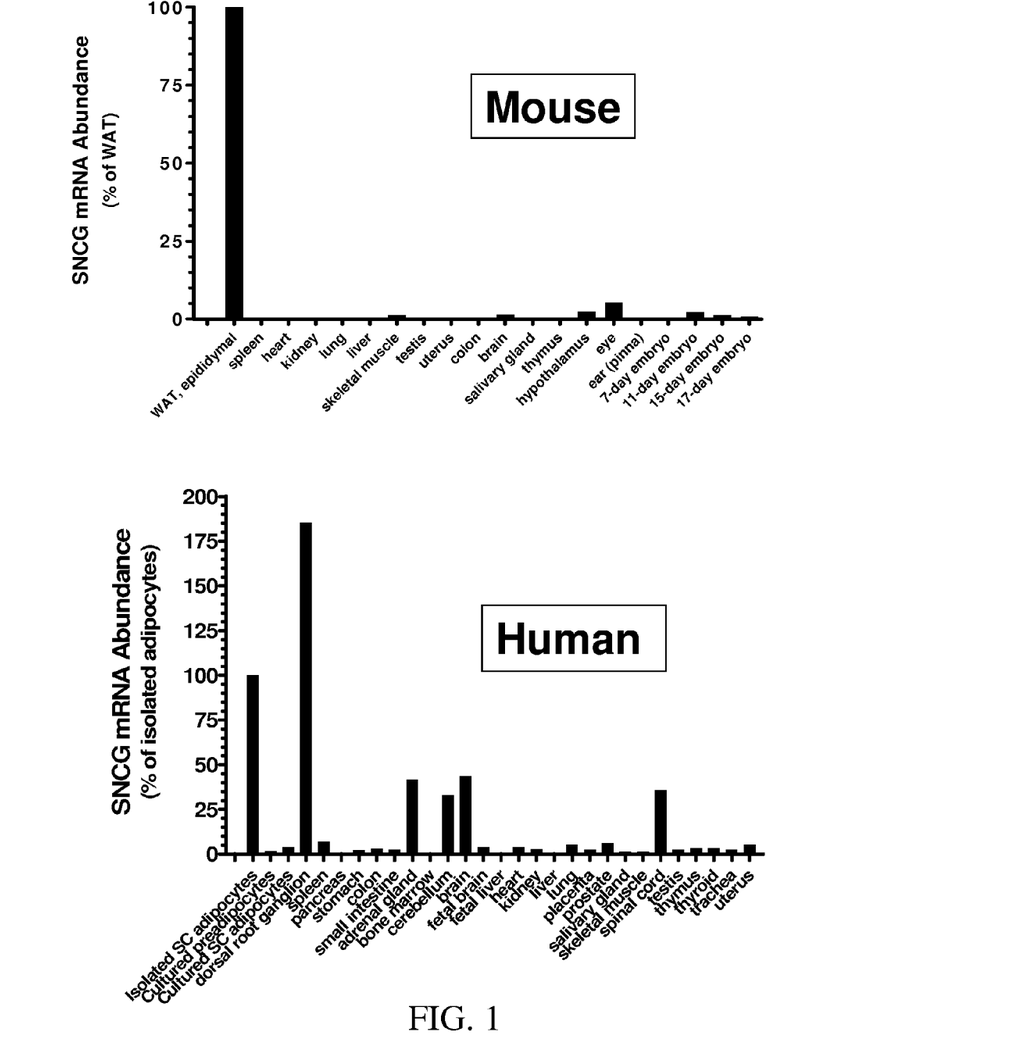
FIG. 1 is a graph of the abundance of γ-synuclein mRNA in human and mouse tissues.
Figure 2:
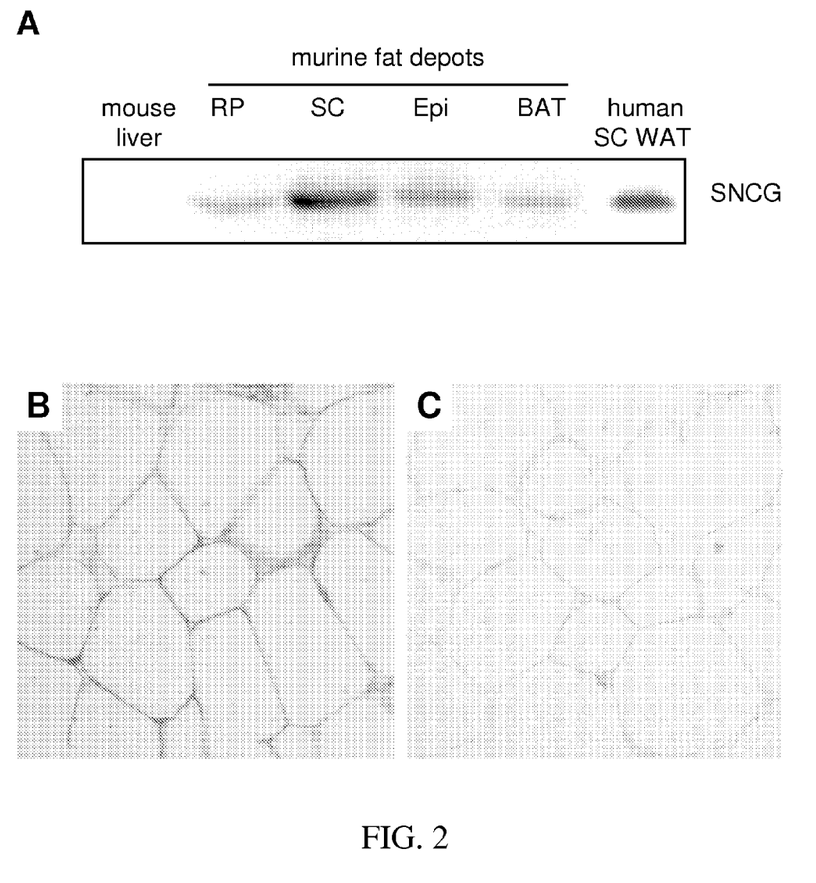
FIG. 2 is a photo of γ-synuclein detected by Western blot analysis in murine and human WAT samples, but not in negative control mouse liver (FIG. 2A); and γ-synuclein protein immunohistochemistry staining patterns in mouse adipocytes (FIGS. 2B and C).
Figure 3:
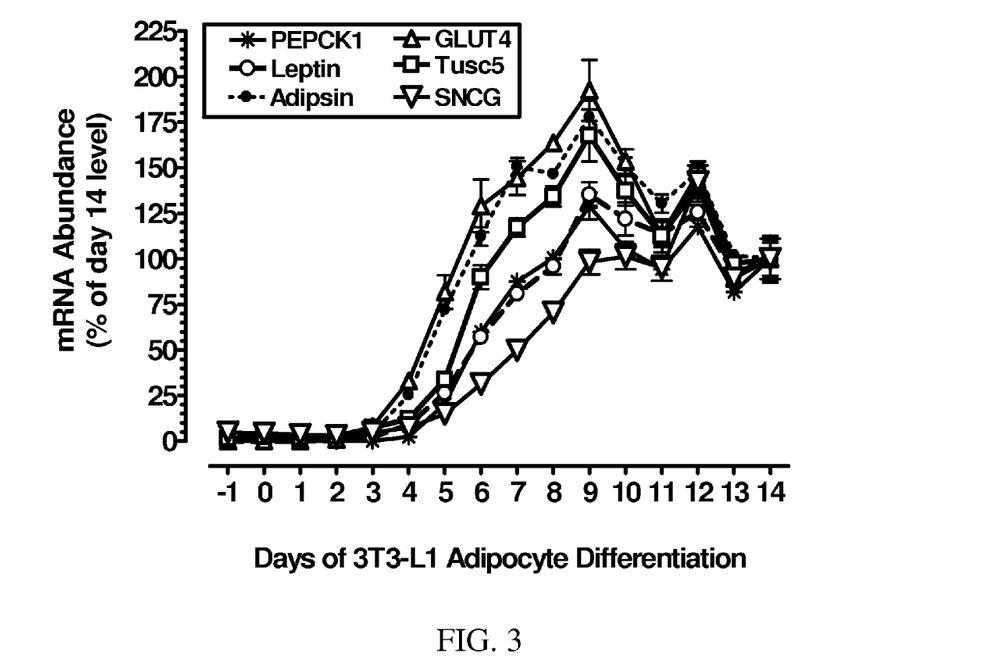
FIG. 3 is a plot of γ-synuclein mRNA expression assayed using the samples t observed for a gene cluster which included Tusc5, PEPCK1, leptin, adipsin, and GLUT4.

Tissue Expression Profile of γ-synuclein. Mouse gene chip tissue expression surveys catalogued in SymAtlas, a public database constructed by the Genomics Institute of the Novartis Research Foundation (GNF, San Diego, Calif.;) (15), were queried to identify genes displaying predominant expression in somatosensory nervous system ganglia (dorsal root ganglia [DRG] and trigeminal ganglia [TG]), WAT, and/or BAT. γ-synuclein, a marker of peripheral neurons and select CNS neurons (16;17;19;20) emerged as one of two genes fitting this pattern (Table 1); the other identified gene was Tusc5. High expression of the gene in murine WAT was confirmed by real-time quantitative PCR (nerve ganglia were unavailable), whereas γ-synuclein mRNA was found to be negligible in other tissues tested (FIG. 1). In humans, γ-synuclein mRNA abundance was highest in the DRG and mRNA prepared from isolated SC adipocytes, with trace to negligible Tusc5 mRNA in most other tissues (including pre-adipocytes) with the exception of spinal cord, brain, cerebellum, and adrenals where levels were ~36%, 43%, 33%, and 42% of adipocytes, respectively (FIG. 1). γ-synuclein protein was readily detected by Western blot analysis in murine and human WAT samples, but not in negative control mouse liver (FIG. 2A); γ-synuclein protein was also observed in retroperitoneal WAT and DRG, but not liver samples, derived from 12 wk old female Zucker rats (data not shown, n=2). Consistent with our observation that γ-synuclein mRNA resides in adipocytes in humans (FIG. 1 and see Results below for Pima Indian subcutaneous adipocytes), γ-synuclein protein appears to be located in mouse adipocytes as judged by immunohistochemistry staining patterns (FIG. 2B).

γ-synuclein mRNA Expression Patterns in Differentiating 3T3-L1 Adipocytes. Determining the time frame over which γ-synuclein is expressed during the 3T3-L1 adipocyte differentiation and maturation program will be useful to understand when γ-synuclein function impacts fat cell physiology. We have previously outlined gene expression clusters in this system for Tusc5 and 24 other adipocyte differentiation and functional markers, and found that the pattern of Tusc5 expression clustered with a group of metabolically-relevant mature adipocyte markers (1). γ-synuclein mRNA expression was assayed using the samples from those experiments, and found to have a pattern consistent with that observed for a gene cluster which included Tusc5, PEPCK1, leptin, adipsin, and GLUT4 (FIG. 3). This suggests that these factors share some gene regulatory elements. Notably, these genes are known to be responsive to insulin, glucose, glucocorticoids, and/or PPARγ agonists.

Figure 4:
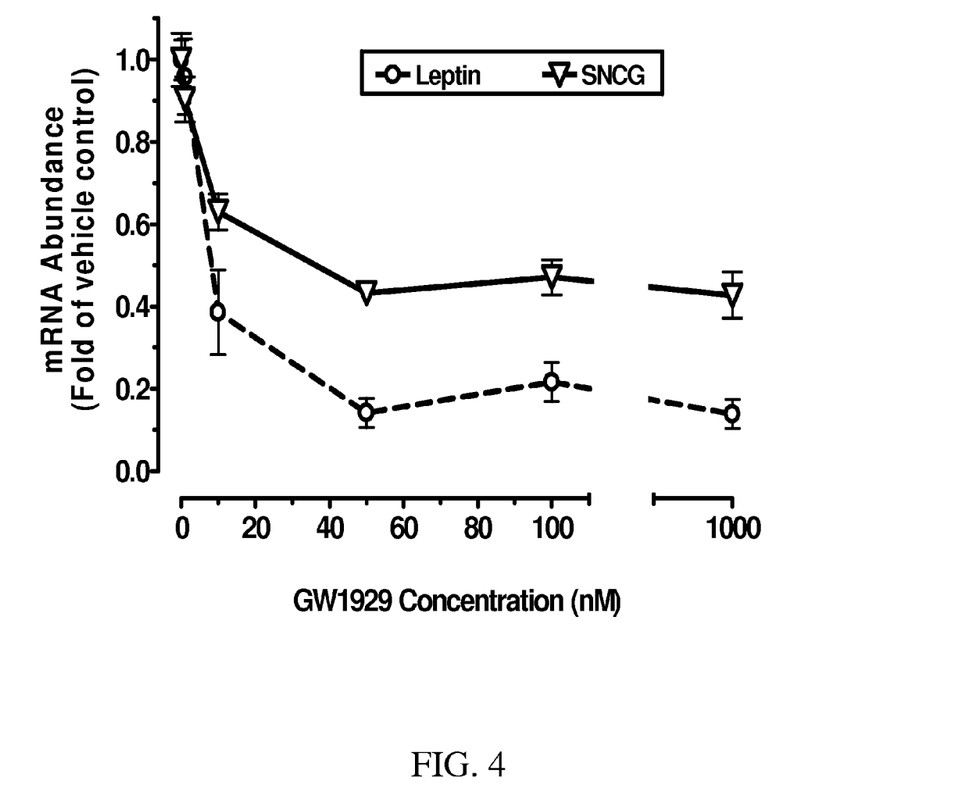
FIG. 4 is a plot of leptin and SNCG mRNA abundance in adipocyte cell line GW1929.

Effects of the PPARγ Agonist GW1929 on Expression Profiles in 3T3-L1 Adipocytes. Many metabolically-relevant adipocyte genes are regulated by PPARγ activities, and PPARγ actions promote entry of developing fat cells into the terminally-differentiated mature adipocyte phenotype. Thus, should γ-synuclein activity be important to adipocyte development and/or metabolism, it is reasonable to consider that the gene would be responsive to PPARγ agonism. In proof-of-concept studies, γ-synuclein mRNA was measured in fully-differentiated 3T3-L1 adipocytes treated for 18 hr with the potent non-thiazoladinedione GW1929, provided at a concentration just above those reported to stimulate in vitro adipocyte glucose uptake and GLUT1 expression (27) and lipogenesis in C3H10T½ cells (23), and at lower concentrations to establish a dose-response. In response to short-term GW1929, γ-synuclein mRNA abundance was decreased by up to ~50% (FIG. 4). This pattern was paralleled qualitatively by that of leptin mRNA (FIG. 4), consistent with the notion that γ-synuclein and leptin could share gene regulatory elements that confer repression following PPARγ activation in fat cells. γ-synuclein and leptin mRNA levels were also decreased by the less potent thiazoladindione troglitazone, but the effective doses required were at least 5-fold higher compared to GW1929 (data not shown). In separate studies, the ability of a single dose of GW1929 to decrease γ-synuclein expression following short-term (18 hr) exposure to the compound was most apparent in mature fat cells, in contrast to pre-adipocytes and immature adipocytes in which γ-synuclein mRNA increased, similar to what was observed for leptin (Supplemental FIG. 1).

Figure 5:
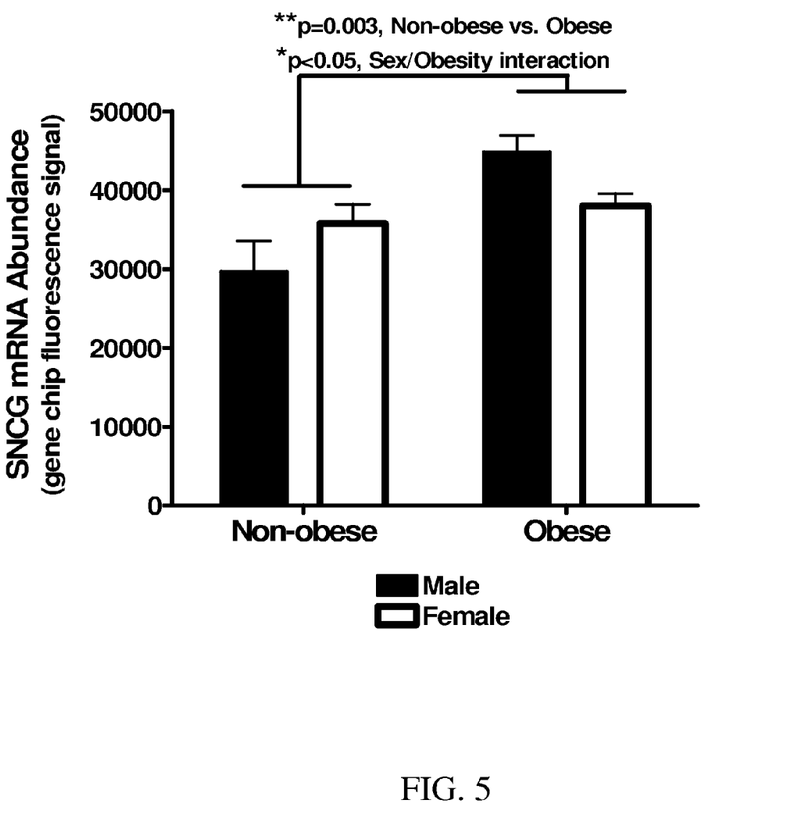
FIG. 5 is plot of the analysis of gene chip raw data confirming that WAT γ-synuclein mRNA levels are significantly increased in obesity.

Effects of Human Obesity and WAT Depot Site on γ-Synuclein mRNA Expression. γ-Synuclein has been implicated as a cancer marker and might be involved in cell survival mechanisms, based on its overexpression in some cancers and studies examining cell death upon titration of γ-synuclein expression in vitro (see Discussion). Thus, we reasoned that in obesity, WAT γ-synuclein expression and activity would be increased since this condition—at least at some stages of its development—is characterized by increased adipocyte proliferation and, potentially, enhanced adipocyte plasticity/turnover to adapt to high caloric load. Consistent with this hypothesis, WAT γ-synuclein transcript levels were significantly increased in obesity in several independent groups of human subjects evaluated. The pattern was initially revealed when the NCBI Gene Expression Omnibus (GEO) gene chip database) was queried to identify studies in which γ-synuclein was differentially-expressed in obesity. It was discovered that γ-synuclein mRNA level appeared to be up-regulated in isolated SC adipocytes derived from obese non-diabetic adult Pima Indians (n=19, 9 males/10 females) compared to non-obese, non-diabetic Pima Indians (n=20, 10 males/10 females) (GEO Accession GSE2508: derived from studies by Permana et al. (28)). Follow-up analysis using the gene chip raw data confirmed that WAT γ-synuclein mRNA levels are significantly increased in obesity, an outcome that is largely influenced by differences between obese and non-obese males (FIG. 5). Consistent with our quantitative RT-PCR human tissue expression profile using unrelated samples (FIG. 1), a GEO query of a second Pima Indian microarray study indicated trace to no expression of γ-synuclein in pre-adipocytes (GEO Accession GSE2510: from (29)).

Figure 6A:
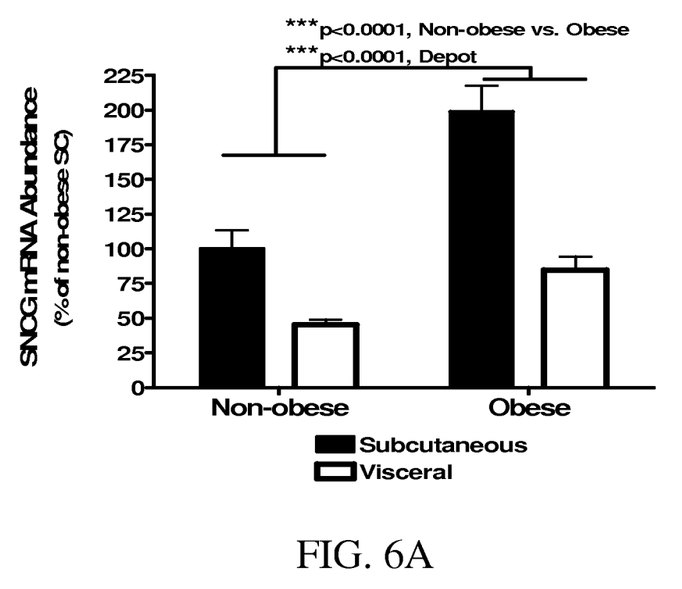
FIG. 6 is a plot comparing γ-synuclein mRNA abundance increased in the SC and VAT of obese compared to non-obese women.
Figure 6B:
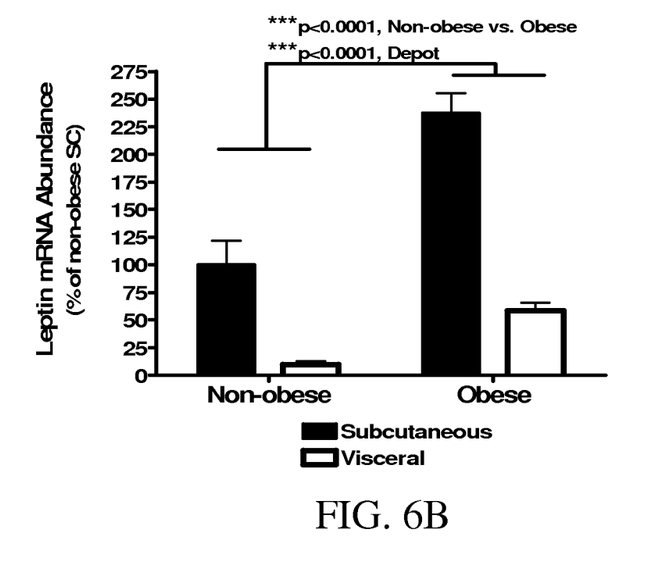
Figure 7:
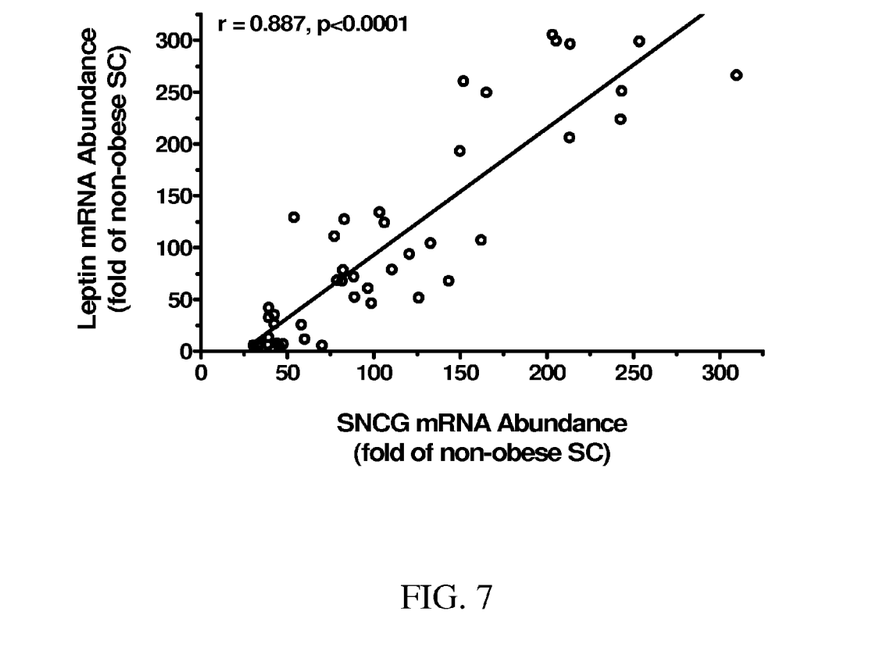
FIG. 7 is a plot of raw data for γ-synuclein and leptin expression in 44 samples (non-obese & obese, VAT & SC.
Figure 8A:
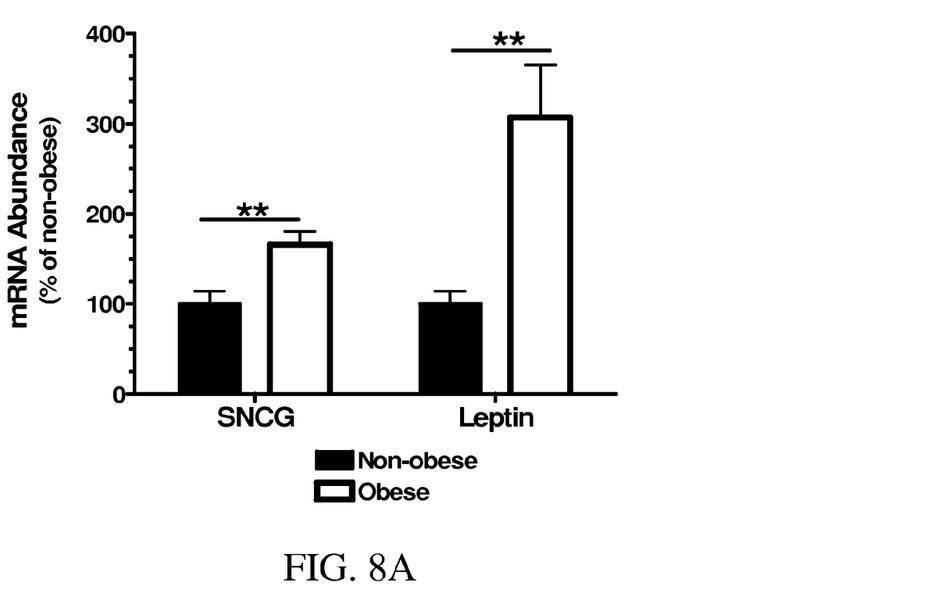
FIG. 8 is a plot of the abundance of γ-synuclein mRNA assayed in SC WAT samples derived from a different cohort of obese and non-obese French women.
Figure 8B:
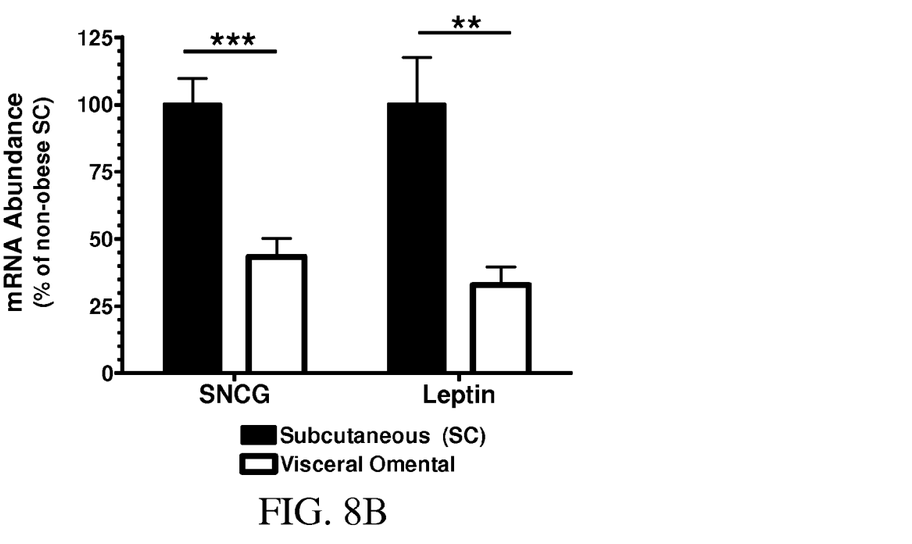
Figure 9:
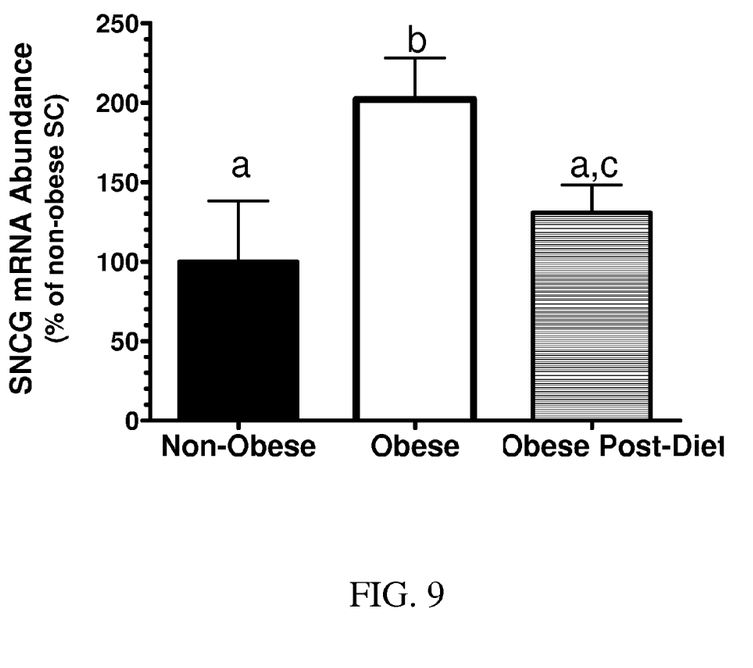
FIG. 9 is a plot of γ-synuclein mRNA levels in obese SC WAT versus non-obese women following 3 weeks of a VLCD regimen.
Figure 10:
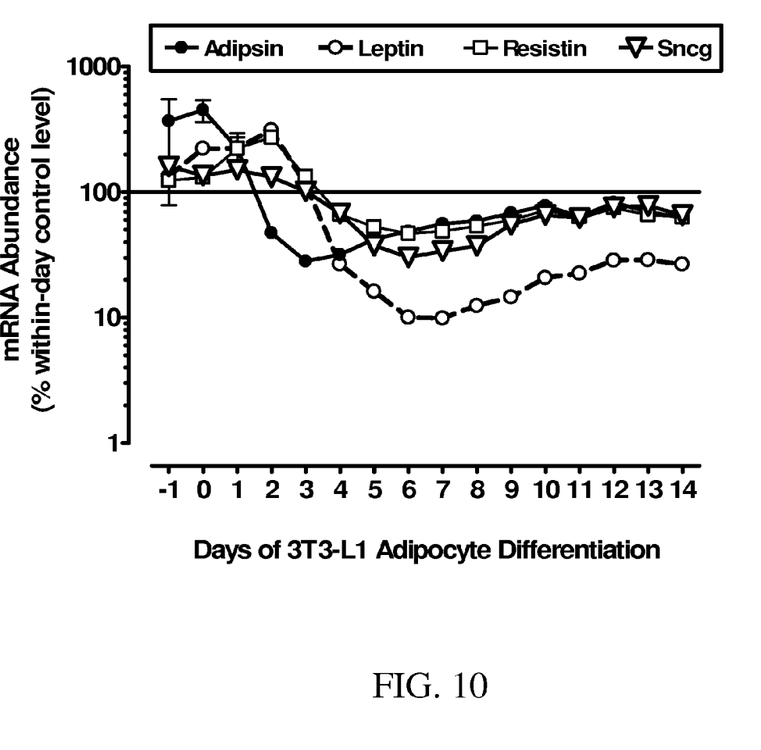
FIG. 10 is a plot of Adipsin, Leptin, Resistin and Sncg mRNA abundance after two weeks of adipocyte differentiation.
Figure 11A:
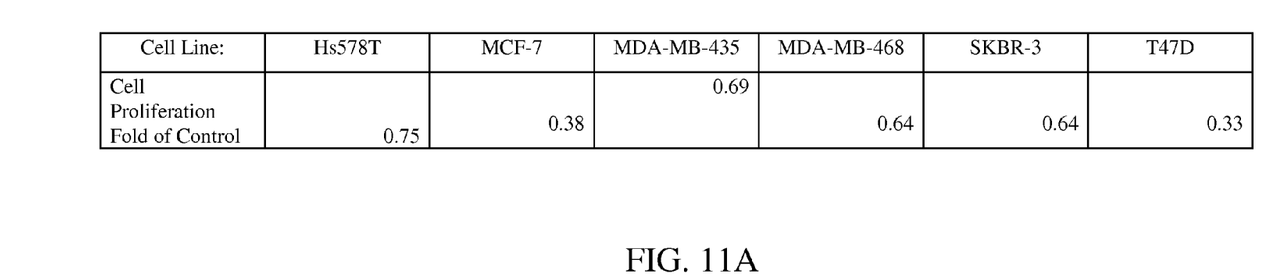
FIG. 11 is a plot of cell proliferation of various adipocyte cell lines.
Figure 11B:
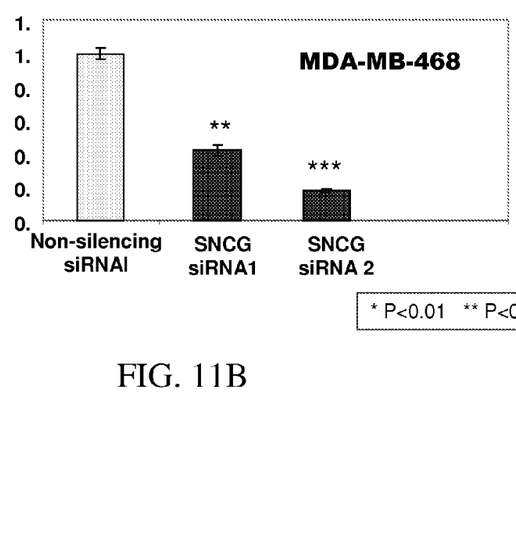
Figure 11C:
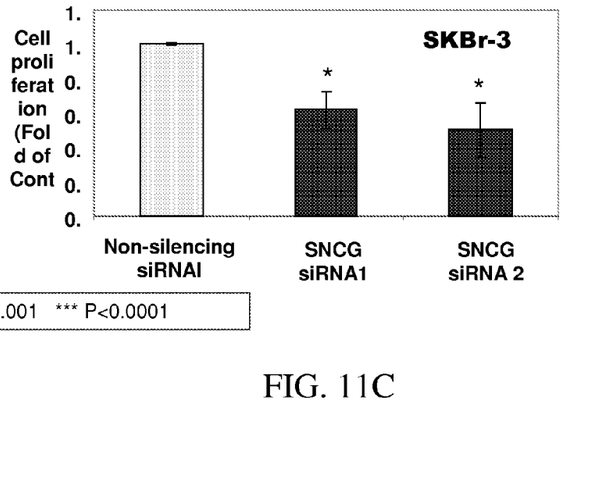

We next examined WAT mRNA samples from a cohort of obese and non-obese French women, previously-described in an expression profile study of adipose 11B-hydroxysteroid dehydrogenase that demonstrated significantly-increased expression of the latter in obesity (24). γ-synuclein mRNA abundance was significantly increased in the SC and VAT of obese compared to non-obese women (FIG. 6A), a pattern also observed for leptin (FIG. 6B). Visceral fat γ-synuclein transcript levels were significantly lower compared to SC in both non-obese and obese groups. Visual analysis of the raw data for γ-synuclein and leptin expression in all 44 samples (non-obese & obese, VAT & SC) suggested coordinate expression of leptin and γ-synuclein, and this was confirmed through correlation analysis which indicated a strong and significant correlation between expression of these genes, regardless of sample source (FIG. 7). The abundance of γ-synuclein mRNA was next assayed in SC WAT samples derived from a different cohort of obese and non-obese French women. Consistent with the results discussed above, expression was significantly increased in obese SC WAT, with a qualitatively similar pattern for leptin mRNA (FIG. 8A). Also consistent was the finding that γ-synuclein and leptin mRNA levels were significantly lower in VAT relative to SC WAT in obese women (FIG. 8B). Interestingly, γ-synuclein mRNA levels that were initially higher in obese SC WAT versus non-obese women were significantly reduced in obese women following 3 weeks of a VLCD regimen (FIG. 9).

What is claimed is:

1. A method for the screening of obesity or obesity-related disorders by identifying in adipocytes γ-synuclein expression as a biomarker for obesity or obesity-related disorders, wherein an increase in γ-synuclein expression is indicative of obesity or obesity-related disorders.

2. The method of claim 1, wherein the obesity-related disorder is selected from the group consisting of cardiovascular disease and diabetes, neuropathy and dementia.

* * * * *